(12) United States Patent
Cho

(10) Patent No.: US 6,379,341 B1
(45) Date of Patent: Apr. 30, 2002

(54) SYRINGE FOR VAGINAL IRRIGATION

(75) Inventor: Young ku Cho, Seoul (KR)

(73) Assignee: Goomi Ehwa Industries Co., Ltd., Kyonggi-do (KR)

( * ) Notice: Subject to any disclaimer, the term of this patent is extended or adjusted under 35 U.S.C. 154(b) by 55 days.

(21) Appl. No.: 09/624,431

(22) Filed: Jul. 24, 2000

(51) Int. Cl.$^7$ .............................................. A61M 31/00
(52) U.S. Cl. ........................ 604/279; 604/142; 604/153
(58) Field of Search ........................... 604/39, 275, 48, 604/279, 217, 142, 212, 132, 153, 37, 295

(56) References Cited

U.S. PATENT DOCUMENTS 6,041,978 A * 3/2000 Hagele ...................... 222/211

FOREIGN PATENT DOCUMENTS

KR           110923      * 11/1997

* cited by examiner

*Primary Examiner*—Brian L. Casler
*Assistant Examiner*—Michelle Lewis
(74) *Attorney, Agent, or Firm*—Merchant & Gould P.C.

(57) ABSTRACT

A syringe for vaginal irrigation is disclosed. This syringe is easily and effectively used for irrigating monstrous secretions from the vagina particularly during or after a menstruation, thus removing monstrous odor from the vagina and allowing the user to feel refreshed at the vagina in addition to keeping the vagina clean and sanitary. The syringe is comprised of an elastic barrel containing a vaginal irrigating solution, an L-shaped elbow pipe engaging with the externally-threaded mouth of the barrel, and a hollow vaginal insert engaging with the elbow pipe through a screw type engagement. This vaginal insert has a linear and tapered profile with the outside diameter of the insert being gradually reduced in a direction from its end around the elbow pipe to its distal end. The vaginal insert also has regularly formed four axial grooves on its external surface, with a plurality of ejection holes being formed along each of the axial grooves and a central ejection hole being formed at the center of the distal end of the insert. The syringe has an L-shaped profile when the barrel, the elbow pipe and the vaginal insert are completely assembled into a single body.

1 Claim, 3 Drawing Sheets

SYRINGE FOR VAGINAL IRRIGATION

BACKGROUND OF THE INVENTION

1. Field of the Invention

The present invention relates to portable-sized and handy syringes for irrigation and, more particularly, to a syringe for vaginal irrigation, designed to be easily and effectively used for irrigating monstrous secretions from the vagina particularly during or after a menstruation, thus removing monstrous odor from the vagina and allowing the user to feel refreshed at the vagina in addition to keeping the vagina clean and sanitary.

2. Description of the Prior Art

During or after a menstruation, monstrous secretions are remained within the vagina, thus causing odor and poor sanitation at the vagina and allowing a woman to feel uncomfortable. In order to overcome such problems caused by the menstruations, most women manually wash their vaginas by hand using irrigating solutions in the prior art. However, such a manual vaginal washing is problematic in that it fails to accomplish a desired vaginal irrigation effect and may cause an infection of the vagina by infectious bacteria of the hands and an injury on the vaginal wall by the fingernails.

In an effort to overcome such a problem experienced in the manual vaginal washing, Korean Laid-open Publication No. 96-3956 discloses a syringe for vaginal irrigation. As shown in FIGS. 3 and 4 of the accompanying drawings, the above conventional syringe for vaginal irrigation comprises an elastic hollow barrel 10 assembled with a removable cap 30 having an irrigation nozzle 20. In the above syringe, the removable cap 30 is designed to assemble the nozzle 20 with the mouth of the barrel 10 in a way such that the nozzle 20 is positioned inside or outside the barrel 10 as desired. When it is necessary to keep the syringe out of use for a period of time, the cap 30 is tightened to the mouth of the barrel 10, with the nozzle 20 positioned inside the barrel 10 so as to be protected from the atmosphere. On the other hand, the cap 30 has to be tightened to the mouth of the barrel 10, with the nozzle 20 positioned outside the barrel 10, when it is necessary to use the syringe. The irrigation nozzle 20 is provided with a plurality of ejection holes 25, 26, 27, 28 and 29 for ejecting an irrigating solution from the barrel 10 into the vagina.

However, the above syringe for vaginal irrigation is problematic in that it has a generally linear shape from the top of the nozzle 20 to the bottom of the barrel 10, and so the syringe does not meet the structure or the posture of the human body during a vaginal irrigation. That is, in order to irrigate the vagina, the syringe for vaginal irrigation is applied to the vagina by a user, with the barrel 10 being gripped by a hand and the nozzle 20 being inserted into the vagina. In such a case, the vagina is nearly positioned vertically, and so the user necessarily grips the syringe almost vertically so as to make the nozzle 20 to be directed upward in an almost vertical direction and inserts the nozzle 20 upward into the almost vertically positioned vagina. After the insertion of the nozzle 20 into the vagina, the barrel 10 is manually compressed by a hand gripping the barrel 10 to eject the vaginal irrigating solution under pressure from the barrel 10 into the vagina through the ejection holes 25 to 29 of the nozzle 20. It is thus very difficult for the user to grip the syringe while irrigating the vagina. In addition, when the barrel 10 is compressed once to eject the irrigating solution into the vagina, the pressurized solution primarily flows from the barrel 10 to the nozzle 20 and is partially ejected into the vagina through the holes 25 to 29 of the nozzle 20. After the first ejection of the pressurized irrigating solution from the nozzle 20 into the vagina, the compressed barrel 10 is released from the compressing force temporarily and expands to restore its original volume before a second ejection of the solution. When the barrel 10 restores its original volume as described above, the remaining solution within the nozzle 20 naturally flows back to the barrel 10 since the syringe is positioned vertically. Such a compressing and releasing action for the barrel 10 has to be repeated several times during a vaginal irrigation process, and so a substantial amount of irrigating solution is not ejected into the vagina, but is finally remained within the barrel 10 and has to be discarded at the end of the vaginal irrigation. This undesirably causes waste of vaginal irrigating solution.

In addition, when it is necessary to use the syringe of FIG. 3 for vaginal irrigation, the cap 30 has to be removed from the mouth of the barrel 10 and is tightened again to the mouth of the barrel 10 with the nozzle 20 positioned outside the barrel 10 as shown in FIG. 4. In such a case, the cap 30 is removed from the mouth of the barrel 10 prior to removing the nozzle 20 from the barrel 10. Thereafter, the nozzle 20 is assembled with the cap 30 in a way such that the nozzle 20 is projected from the top surface of the cap 30. After assembling the nozzle 20 with the cap 30, the cap 30 is fully tightened again to the mouth of the barrel 10 with the nozzle 20 positioned outside the barrel 10 as shown in FIG. 4. After a desired vaginal irrigation is accomplished, the nozzle 20 has to be changed from the position of FIG. 4 to the position of FIG. 3 by handling the cap 30 and nozzle 20 along with the barrel 10 through a process inverse to that described above. In a brief description, the above syringe for vaginal irrigation forces a user to disassemble and assemble the parts of the syringe before and after every vaginal irrigation, and so said syringe is very inconvenient to users.

Another problem, experienced in the above syringe for vaginal irrigation, resides in that the nozzle 20 has a structural defect. That is, the nozzle 20 is gradually reduced in its diameter in a direction from the outside end to the inside end, and so the labium is expanded in its diameter to allow an insertion of the large-diameter outside end of the nozzle 20 into the vagina through the labium. However, when the nozzle 20 is fully inserted into the vagina, the labium cannot quickly shrink, and so it fails to closely surround the small-diameter inside end of the nozzle 20, thus remaining a gap between the nozzle 20 and the labium. Therefore, the irrigating solution undesirably flows from the vagina to the outside through the gap and contaminates the hands and the barrel 10, and so the syringe regrettably makes a user feel unpleasant during a vaginal irrigation.

SUMMARY OF THE INVENTION

Accordingly, the present invention has been made keeping in mind the above problems occurring in the prior art, and an object of the present invention is to provide a syringe for vaginal irrigation, which is easily and effectively used for irrigating monstrous secretions from the vagina particularly during or after a menstruation, thus removing monstrous odor from the vagina and allowing the user to feel refreshed at the vagina in addition to keeping the vagina clean and sanitary.

Another object of the present invention is to provide a syringe for vaginal irrigation, which has a portable and handy size and accomplishes a desired vaginal irrigation effect, and is easily produced through a simple production process in addition to allowing a user to easily and simply assemble and disassemble the parts of the syringe.

In order to accomplish the above object, the present invention provides a syringe for vaginal irrigation, comprising: an elastic barrel containing a vaginal irrigating solution therein, the barrel having an externally-threaded mouth; an L-shaped elbow pipe engaging with the externally-threaded mouth of the barrel at the first end thereof, the first end of the elbow pipe being internally threaded so as to engage with the externally-threaded mouth of the barrel, the elbow pipe being also externally threaded at its second end; and a hollow vaginal insert engaging with the externally-threaded second end of the elbow pipe through a screw type engagement, the vaginal insert having a linear and tapered profile with the outside diameter of the insert being gradually reduced in a direction from its first end around the second end of the elbow pipe to its second end, the vaginal insert having regularly formed four axial grooves on its external surface in an extent from its middle portion to its second end, with a plurality of side ejection holes being formed along each of the axial grooves and a central ejection hole being formed at the center of the second end of the insert, whereby the syringe has an L-shaped profile when the barrel, the elbow pipe and the vaginal insert are completely assembled into a single body.

BRIEF DESCRIPTION OF THE DRAWINGS

The above and other objects, features and other advantageous of the present invention will be more clearly understood from the following detailed description taken in conjunction with the accompanying drawings, in which.

DETAILED DESCRIPTION OF THE INVENTION

Figure 1:
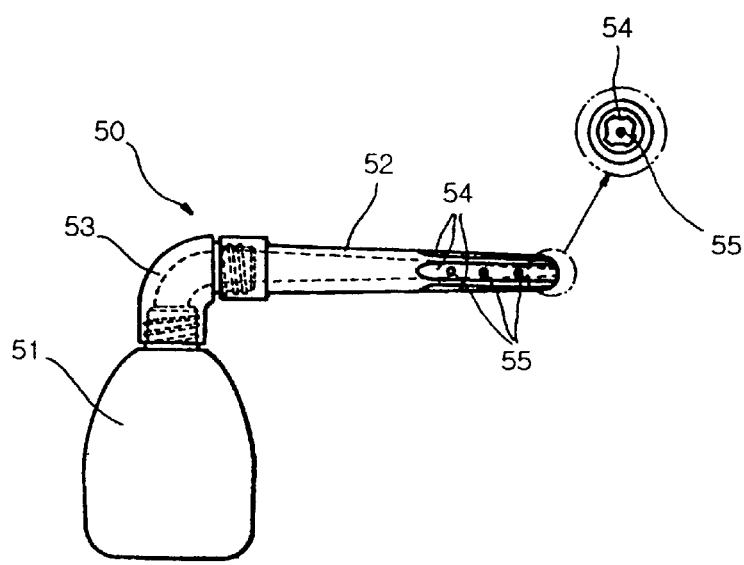
FIG. 1 is a front view of a syringe for vaginal irrigation in accordance with the preferred embodiment of the present invention.
Figure 2:
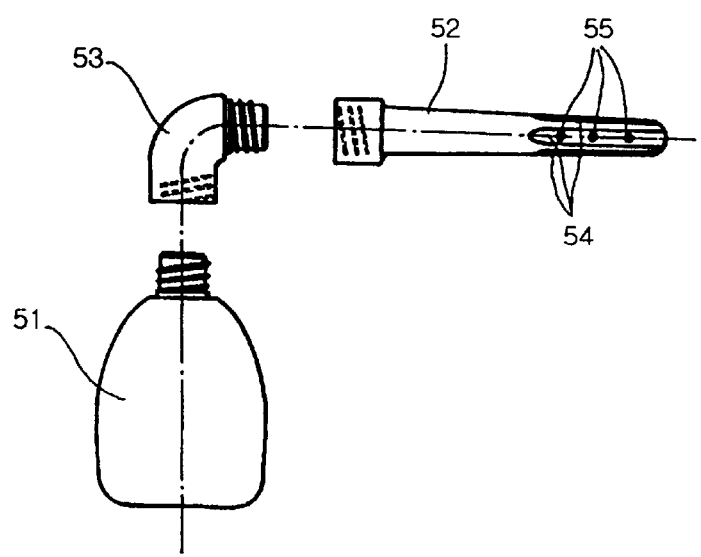
FIG. 2 is an exploded perspective of the syringe of FIG. 1.
Figure 3:
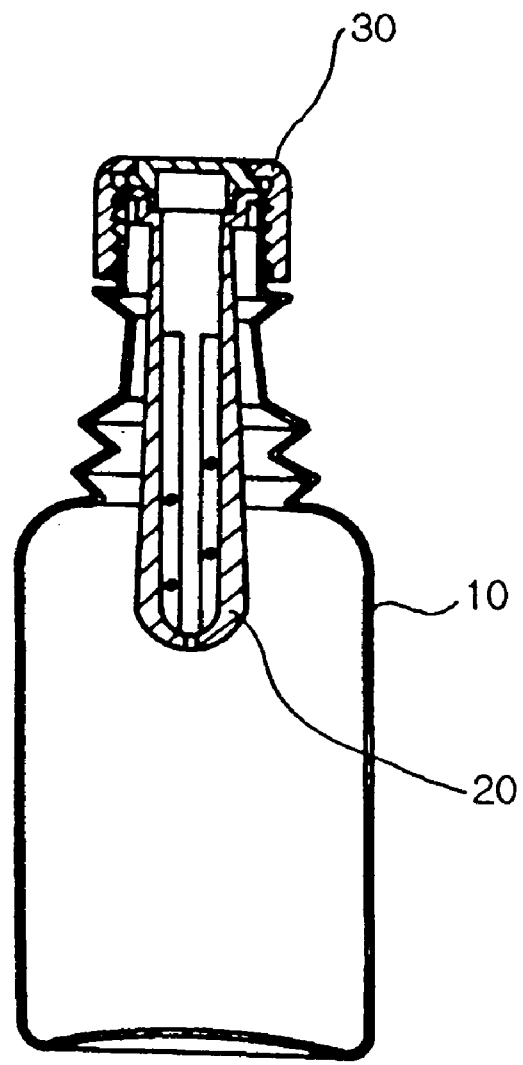
FIG. 3 is a sectional view of a conventional syringe for vaginal irrigation, when a removable cap of the syringe is tightened to the mouth of a hollow barrel with a nozzle of the cap being positioned inside the barrel.
Figure 4:
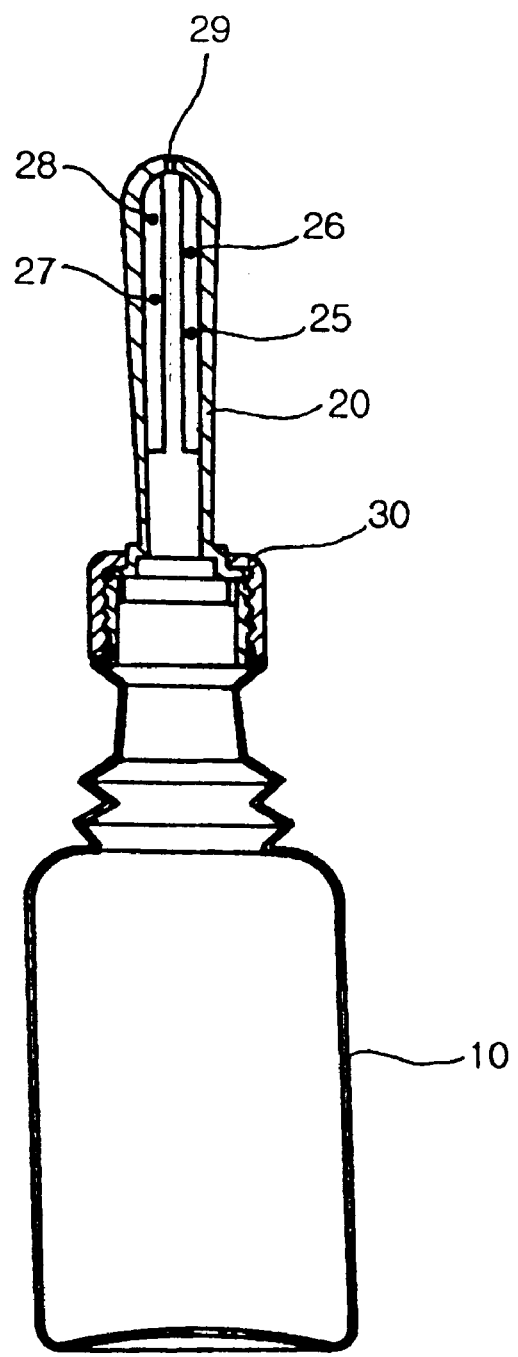
FIG. 4 is a sectional view of the conventional syringe of FIG. 3, when the removable cap of the syringe is tightened to the mouth of the barrel with the nozzle being positioned outside the barrel.

FIG. 1 is a front view of a syringe for vaginal irrigation in accordance with the preferred embodiment of the present invention. FIG. 2 is an exploded perspective of the syringe of FIG. 1.

As shown in the drawings, the vaginal irrigation syringe 50 of this invention comprises an elastic barrel 51 containing a vaginal irrigating solution therein. This barrel 51 has an externally-threaded mouth. An L-shaped elbow pipe 53 engages with the externally-threaded mouth of the barrel 51 at the first end thereof. This first end of the elbow pipe 53 is internally threaded so as to engage with the externally-threaded mouth of the barrel 51. The above elbow pipe 53 is also externally threaded at its second end. The syringe 50 also comprises a hollow vaginal insert 52, which engages with the externally-threaded second end of the elbow pipe 53 through a screw type engagement. This vaginal insert 52 has a linear and tapered profile, with the outside diameter of the insert 52 being gradually reduced in a direction from its first end around the second end of the elbow pipe 53 to its second end. The above vaginal insert 52 also has regularly formed four axial grooves 54 on its external surface in an extent from its middle portion to its second end, with a plurality of side ejection holes 55 being formed along each of the axial grooves 54 and one central ejection hole 55 being formed at the center of the second end of the insert 52.

In order to irrigate the vagina using the syringe 50 of this invention to remove monstrous secretions from the vagina particularly during or after a menstruation, a desired vaginal irrigating solution is primarily contained in the barrel 51 to a predetermined level. Thereafter, the elbow pipe 53 engages with the externally-threaded mouth of the barrel 51 at its internally-threaded first end prior to bringing the internally-threaded first end of the hollow vaginal insert 52 into screw type engagement with the externally-threaded second end of the elbow pipe 53. When the barrel 51, the elbow pipe 53 and the vaginal insert 52 are completely assembled into a desired L-shaped syringe 50, the syringe is applied to the vagina by inserting the vaginal insert 52 into the vagina prior to performing desired vaginal irrigation. In such a case, since the vaginal insert 52 has a linear and tapered profile with the outside diameter being gradually reduced in a direction from its first end around the second end of the elbow pipe 53 to its second end, the first end portion of the insert 52 is closely surrounded by the labium after the insert 52 is fully inserted into the vagina.

As described above, the syringe 50 of this invention has an L-shaped profile when the barrel 51, the elbow pipe 53 and the vaginal insert 52 are completely assembled into a single body. When the insert 52 is inserted into the vagina with the barrel 51 being gripped by a hand during vaginal irrigation, the barrel 51 is in its completely overturned position, and so the syringe 50 does not force a user to inconveniently bend her wrist while gripping the barrel 51, but allows the user to conveniently grip and manipulate the barrel 51 while irrigating the vagina. Such a completely overturned position of the barrel 51 also allows the vaginal irrigating solution to naturally flow from the barrel 51 to the mouth due to gravity, and so the solution can be almost completely ejected from the barrel 51 without being left within the barrel 51.

In addition, the vaginal insert 52 forms desired spaces between its axial grooves 54 and the vaginal wall. When the barrel 51 is compressed by a hand, the irrigating solution under pressure flows from the mouth of the barrel 51 to the vaginal insert 52 through the elbow pipe 53 prior to being ejected from the insert 52 into the vagina through both the central ejection hole 55 formed at the second end of the insert 52 and the side ejection holes 55 formed along the grooves 54 of the insert 52. Due to such an ejection of pressurized irrigating solution into the vagina, it is possible to easily and effectively irrigate monstrous secretions from both the vaginal wall and the vaginal canal. In such a case, the monstrous secretions removed from both the vaginal wall and the vaginal canal flow down along with the irrigating solution to the area inside the labium. However, since the large-diameter first end portion of the insert 52 around the elbow pipe 53 is closely surrounded by the labium, the secretions along with the solution do not flow from the vagina to the outside through the labium until the insert 52 is completely removed from the vagina after the vaginal irrigation. Therefore, the syringe 50 of this invention does not contaminate the hands or the barrel 10 by the secretions, and so it allows a user feel less unpleasant while irrigating the vagina.

As described above, the syringe for vaginal irrigation of this invention comprises three parts: an elastic barrel, an L-shaped elbow pipe and a vaginal insert, and so the syringe is easily and simply produced, assembled and disassembled. After the syringe of this invention is used once for vaginal irrigation, the vaginal insert is removed from the syringe and is completely disinfected and sterilized prior to being used again. Therefore, the syringe is advantageous in that it is easily and simply used, disinfected and sterilized. In addition, since the syringe of this invention is easily and simply produced, it is possible to reduce the production cost of such syringes for vaginal irrigation and to provide inexpensive syringes to consumers.

In addition, the syringe has an L-shaped profile when the barrel, the elbow pipe and the vaginal insert are completely assembled into a single body. Therefore, when the insert is inserted into the vagina with the barrel being gripped by a hand during a vaginal irrigation, the barrel is in its completely overturned position. The syringe does not force a user to inconveniently bend her wrist while gripping the barrel, but allows the user to conveniently grip and manipulate the barrel. The completely overturned position of the barrel also allows the vaginal irrigating solution to naturally flow from the barrel to the mouth due to gravity, and so the solution can be almost completely ejected from the barrel without being left within the barrel. This syringe thus conserves the vaginal irrigating solution.

The vaginal insert also has a linear and tapered profile with the outside diameter being gradually reduced in a direction from its first end around the second end of the elbow pipe to its second end. Therefore, the vaginal insert is easily inserted into the vagina during a vaginal irrigation. In addition, the large-diameter first end portion of the vagina insert is closely surrounded by the labium during a vaginal irrigation, and so the secretions along with the solution do not flow from the vagina to the outside through the labium until the insert is completely removed from the vagina after the vaginal irrigation. The syringe of this invention does not contaminate the hands or the barrel by the secretions, thus allowing a user to sanitarily use the syringe while feeling less unpleasant during a vaginal irrigation.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. A syringe for vaginal irrigation, comprising:
    an elastic barrel containing a vaginal irrigating solution therein, said barrel having an externally-threaded mouth;
    an L-shaped elbow pipe engaging with said externally-threaded mouth of the barrel at a first end thereof, said first end of the elbow pipe being internally threaded so as to engage with the externally-threaded mouth of the barrel, said elbow pipe being also externally threaded at its second end; and
    a hollow vaginal insert engaging with the externally-threaded second end of the elbow pipe through a screw type engagement, said vaginal insert having a linear and tapered profile with an outside diameter of the insert being gradually reduced in a direction from its first end around the second end of the elbow pipe to its second end, said vaginal insert having regularly formed four axial grooves on its external surface in an extent from its middle portion to its second end, with a plurality of side ejection holes being formed along each of said axial grooves and a central ejection hole being formed at a center of said second end of the insert,
    whereby the syringe has an L-shaped profile when the barrel, the elbow pipe and the vaginal insert are completely assembled into a single body.

* * * * *